United States Patent [19]

Davis et al.

[11] Patent Number: 5,637,873
[45] Date of Patent: Jun. 10, 1997

[54] DIRECTIONAL REFLECTOMETER FOR MEASURING OPTICAL BIDIRECTIONAL REFLECTANCE

[75] Inventors: Keith J. Davis, Issaquah; Diane C. Rawlings, Bellevue, both of Wash.

[73] Assignee: The Boeing Company, Seattle, Wash.

[21] Appl. No.: 484,576

[22] Filed: Jun. 7, 1995

[51] Int. Cl.$^6$ .............................. G01J 5/02; G01N 21/47
[52] U.S. Cl. .................... 250/339.11; 250/341.8; 250/352; 356/51; 356/446
[58] Field of Search .................... 356/445–448; 250/341.8, 339.11, 372, 352; 359/857–859, 861, 864, 869

*Primary Examiner*—Frank Gonzalez
*Assistant Examiner*—Jason D. Eisenberg
*Attorney, Agent, or Firm*—John C. Hammar

[57] ABSTRACT

The present invention is a directional reflectometer that measures the optical bidirectional reflectance distribution function [BRDF] of a surface in situ on a finished article, e.g. a vehicle, to provide information on its surface emissivity. The light wavelength may be IR, near-IR or visible. Light, preferably focused to a small spot on the surface, is projected onto the surface at an angle adjustable in azimuth and elevation. A wide angle mirror and/or lens system transfers light scattered from the surface onto an imaging sensor, preserving scattering angle information and thereby permitting the BRDFs for a given incidence angle and all scattering angles to be measured simultaneously. A hand held or laptop computer sets the incidence angle, reads the sensor outputs and renders judgments on the quality of the surface in a factory or field environment.

9 Claims, 5 Drawing Sheets

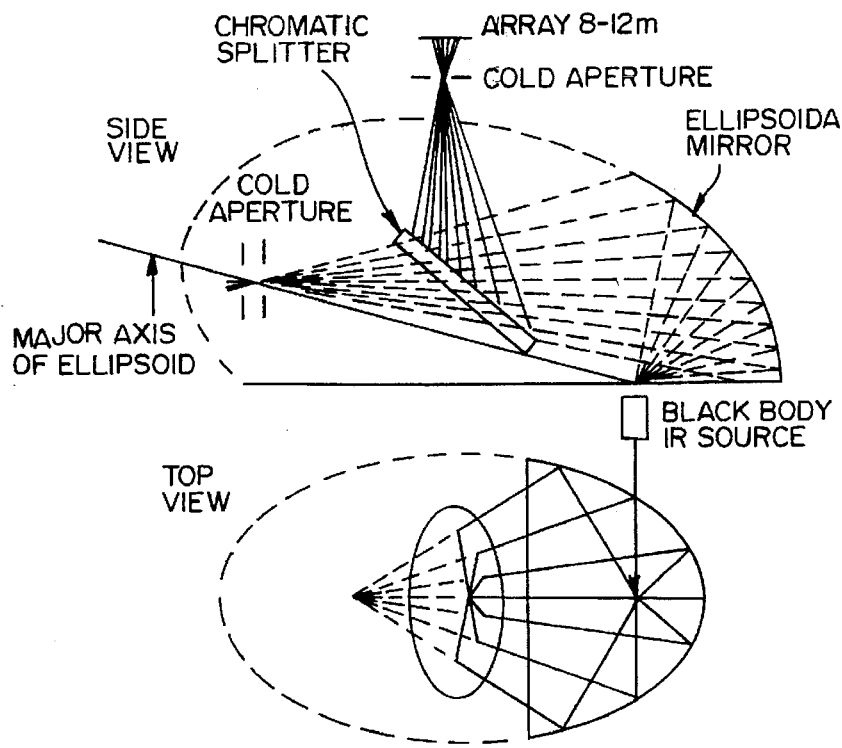
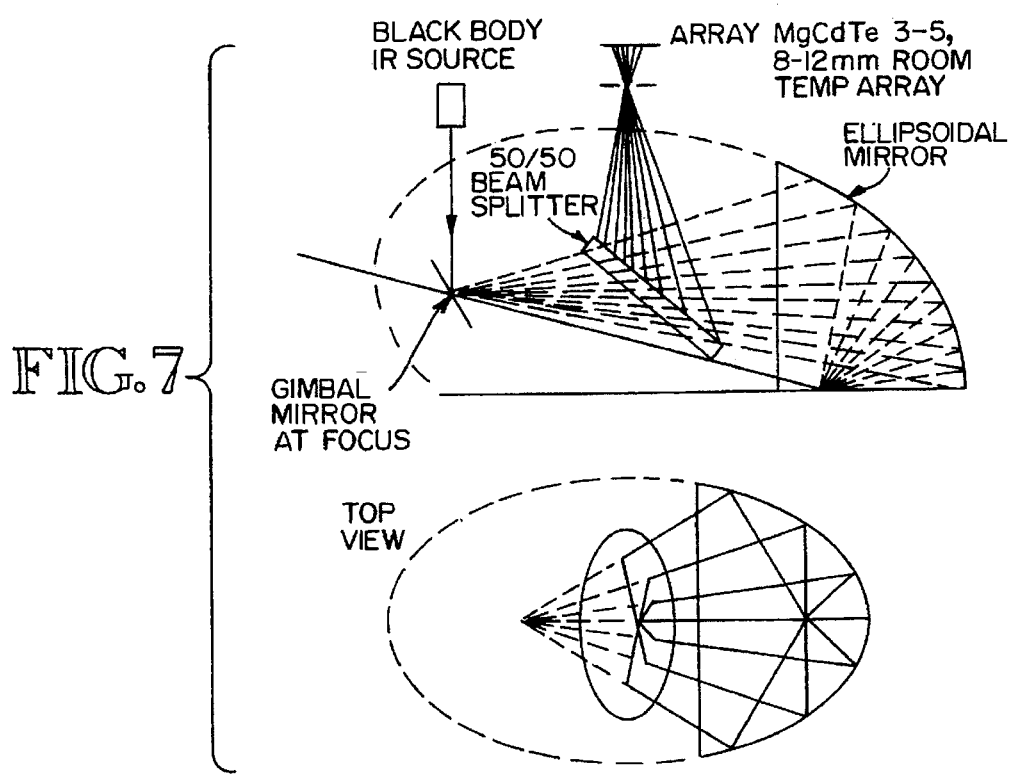

DIRECTIONAL REFLECTOMETER FOR MEASURING OPTICAL BIDIRECTIONAL REFLECTANCE

TECHNICAL FIELD

The present invention is an apparatus for laboratory or field measurement of the optical UV, visible, and IR bidirectional reflectance to determine the quality of a surface, measuring full-hemisphere, nonintegrated directional reflectance of applied coatings.

BACKGROUND ART

It is difficult to accurately measure the emissivity or reflectivity of a surface especially at low grazing angles, but the need for reliable measurements is ever increasing, especially for military vehicles where these physical characteristics (and their control) are significant features for survival with respect to detection with modem optical (infrared {IR} and visible) seekers. Today, measurements of an entire vehicle are difficult, expensive, and require a carefully controlled or measured environment.

The present invention addresses a need to measure that IR directional emissivity and reflectivity of surfaces and coatings. The emissivity and bidirectional reflectivity play a major role in determining an airframe's total IR signature. Coatings are often designed to produce particular emissivity/reflectivity characteristics. While techniques exist to measure these properties for small samples in the laboratory, none of these methods are suitable for measuring the properties of the coatings once they are applied to a large airframe.

In U.S. patent application Ser. No. 08/184,556, we described a laboratory emissometer for measuring the emissivity of sample coatings. This device is useful only for small samples and is not suitable for measuring the signature of a surface or vehicle. It is, nevertheless, a useful tool for designing coatings. The emissometer operates by measuring the radiation eminating from the surface because of its temperature. This device is capable of measuring the emittance from normal to the surface (0°) to a grazing angle of about 800° off the normal spectrally and as a function of temperature between −65° F. and 400° F.

Surface Optics markets a protable measurement device that operates in the IR.

Modern aircraft have specifications and requirements for emissivity and reflectivity (based on the IR signature goals) that present new issues relative to the inspection techniques and tools required for manufacturing and maintenance. In particular, the IR signature is affected by the exterior coating reflectance and emittance. The performance of the coating can be sensitive to variations in the coating materials, application processes, and to environmental exposure. To assure that an aircraft meets IR specifications, IR coating performance must be tested as applied on the air vehicle surface. Such measurements must be repeated on a regular maintenance schedule and after repairs to assure continuing signature performance of the aircraft. These measurements must be nondestructive, rapid, and require minimal skill level and training. Measurement devices should be easily portable (hand-held if possible), affordable, rugged, and require little support (standard power, room temperature detectors).

NDE (nondestructive evaluation) measurements must provide sufficient information to assess whether the surface meets coating and vehicle specifications. It is important that the information be of sufficient content and quality, without incurring costs associated with collecting unused information. In addition, the instrument must be able to collect data and indicate pass/fail to the operator.

SUMMARY OF THE INVENTION

The directional reflectometer of the present invention is a compact system for measuring emissivity/reflectivity of coatings applied to laboratory coupons or to large objects which are not amenable to testing in the laboratory. The intended role is for quality assurance during manufacturing and in field service to verify that coatings are performing properly. The invention also enables a significant advancement in the laboratory measurement of surfaces because it provides a rapid and intuitive means of understanding the directionality of measured surfaces. We use reflective and refractive optics to form an "image" of the angular distribution of light reflecting from the surface of interest. Our concept allows virtually all of the IR light leaving a surface to be collected onto a single imaging array or possibly non-imaging detector.

The reflectometer is a small, traveling, broadband IR (3–12 μm) device or a UV, visible, and near IR (0.3–3 μm) device which is attached to a computer. The computer analyzes the data collected at the imaging array and presents it in several formats, most notably a "pass-fail." In this device (1) reflection is measured at incident and reflected angles between near-normal and grazing (up to 88° from normal), (2) an angle-space "image" is formed of the scattered radiation, providing full directional reflectance information at a glance, and (3) the rapid response of this type of system allows data to be collected continuously as the device is moved across a surface. The angle-space "image" contains enough information to assess both standard and special surfaces or coatings and can be integrated to determine total hemispherical reflectance. Personal or laptop computer-based analysis permits rapid determination of pass-fail responses.

BRIEF DESCRIPTION OF THE DRAWINGS

FIGS. 3A and 3B are taken from the plane of incidence, line A—A in FIG. 2, while FIG. 3C is taken from the plane of the source and radiant beam, line C—C in FIG. 2.

FIGS. 6 & 7 are variations of the reflectometer of FIG. 2.

DETAILED DESCRIPTION OF THE PREFERRED EMBODIMENT

Figure 1:
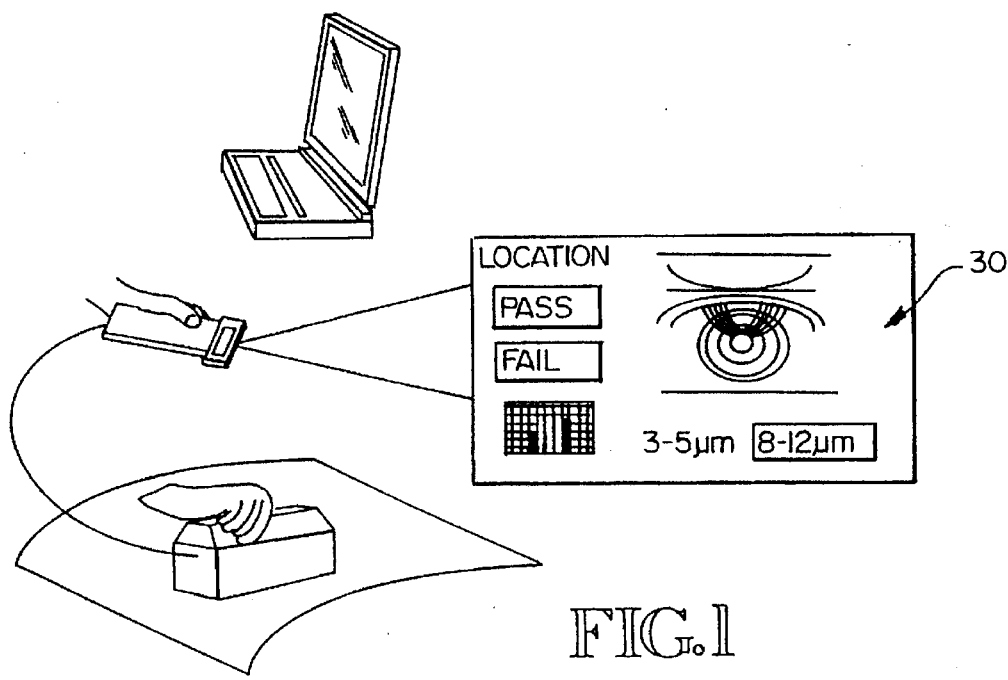
FIG. 1 is a schematic of the directional reflectometer of the present invention including an enlarged illustration of the screen display.

The directional reflectometer of the present invention measures the optical bidirectional reflectance of a surface to provide the reflectivity and estimated emissivity. The device is small, portable, and potentially provides either broadband (3-12 μm) or spectral reflectance between near normal and grazing angles permitting pass-fail assessment of surface quality in the field.

Before describing the device, first we will discuss the significance of the measurements that the device allows us to make.

Both emission and reflection information are used to determine aircraft signature in conjunction with assumptions regarding the vehicle mission, flight environment, and speed. Requirements to measure reflectance vary from relatively simple to complex depending on the surface materials and the vehicle specification. Typically, directional hemispherical reflectance measurements (specular and diffuse) are used for routine measurements, and selected bidirectional reflectance (BDR) measurements are used for special purposes such as determining contamination or degree of damage on highly specular surfaces. The combination of these measurements provides the desired information for most surfaces, however, the measurement of full bidirectional reflectance distribution functions (BRDF) can consume days per sample and therefore is not useful for manufacturing quality control, maintenance, inspection or post-repair inspection of air vehicles. For NDE applications a much simpler, cost-effective method is needed.

Emittance would be difficult and costly to measure on an aircraft surface because of the necessity to control and know surface temperature accurately. Therefore, emittance is often calculated from the total bidirectional hemispherical reflectance assuming the validity of Kirchoff's law. This law states that if a blackbody and an arbitrary body are in thermal equilibrium, the absorptivity ($\alpha$) integrated over all wavelengths is equal to the emissivity ($\epsilon$) integrated over all wavelengths. It can also be shown that this equality is true at each wavelength ($\alpha(\lambda)=\epsilon(\lambda)$) where the temperature of each body is the same. The Total Power Law states that when radiation is incident on a body, the sum of the absorbed radiation, the reflected radiation, and the transmitted radiation is equal to unity ($\alpha+\rho+\tau=1$). This Total Power Law relationship is also true for specific wavelengths ($\alpha(\lambda)+\rho(\lambda)+\tau(\lambda)=1$). When Kirchoff's law is combined with the Total Power Law, and the surface is assumed to be opaque ($\tau=0$) and in an isotropic radiative environment, and at a uniform temperature, the emissivity is equal to one minus the reflectivity ($\epsilon=1-\rho$ or $\epsilon(\lambda)=1-\rho(\lambda)$). These equations also are true for specific angles of view ($\theta,\phi$), but generally are not hue for the two different components of polarization.

Making these assumptions, directional emittance is calculated from direction hemispherical reflectance which is typically measured using one of the three following methods.

1.) Illuminating at a specific angle of interest ($\theta,\phi$) and detecting hemispherically, typically by using an integrating sphere. Most total hemispherical reflectance measurements are made in this manner using angles of incidence near normal. Care must be taken in these measurements when measuring at incident angles of greater than 50°. If the sample surface is placed at the center of the sphere, it is not possible to measure an extended surface. If the material to be measured is placed on the integrating sphere wall, extended surfaces can be measured, however, the angle of incidence is limited clue to the inability to place the source at near grazing incidence without illuminating the sphere wall directly or without bumping the source into the surface.

2.) Illuminating hemispherically and collecting radiation spectrally or band-averaged at the specific angle of interest for emission ($\theta,\phi$). An example of this type of system has been built by Surface Optics Corporation using a blackbody source at one focus of an ellipse and the sample at the other focus. The detector is moved between 10° and 80° off normal. This type of measurement provides an integrated directional reflectance, however, all information is lost relating to the angular distribution of the reflected radiation. Angular distribution is important to know, as air vehicle IR specifications are written for threat defeat over a range of angles.

3.) Integrating the bidirectional scatter measured over the hemisphere for a particular incident angle ($\theta,\phi$). This integration is a time consuming measurement and the numerical integration to produce a total hemispherical reflectance includes the summation of many sources of error resulting in inaccurate data and conclusions.

None of these methods are known to be commercially available as hand-held devices in the infrared, except for the Surface Optics device mentioned earlier. Small hand-held reflectance devices for NDE are fairly common in the visible range and are used for measuring color or contamination. For example, Toomay Mathis provides small hand-held scatterometers which detect the bidirectional scatter at particular incident and detection angles. Bidirectional scatter measurements such as these are limited for the purpose of evaluating signature-related performance because there is no measurement or integration of the total reflected energy, only specific (and limited) information about the directional scatter.

In summary, existing devices and measurement methods fall short of the need for NDE because they are not typically designed for measurements in the IR at the angles of interest, nor are they designed for NDE use (measurement times are too long), or the optical design does not permit viewing of an extended surface (limitations on sample size and curvature). In addition, no existing system will provide both directional scatter information (important for reflected contributions to the IR signature) and a total hemispherically integrated reflectance (important for calculating the emitted contribution to the signature).

In contrast to previous approaches, our proposed concept provides: (1) the ability to measure at incident angles of up to 80° or greater off normal, and (2) the ability to determine both an integrated total hemispherical reflectance with greater throughput than measurements using integrating spheres and an image of the scattered intensity over a hemisphere (some of our designs under consideration require an internal or external rotation of 180° to collect full hemispherical information for non-isotropic samples).

Our device 100 for measuring the hemispherical reflectance forms a video "image" of the angular distribution of the specularly and diffusely reflected radiation. Our baseline design concept, illustrated in FIG. 2, uses the imaging properties of an ellipsoidal reflector 10. Light diverging from one focus 12 of the ellipse is specularly reflected and converges towards the second focus 14, but is redirected by a secondary mirror 16. In our configuration, the major axis 18 which passes through the foci 12 & 14, is tilted relative to the sample surface to facilitate the collection of grazing rays.

Figure 3:
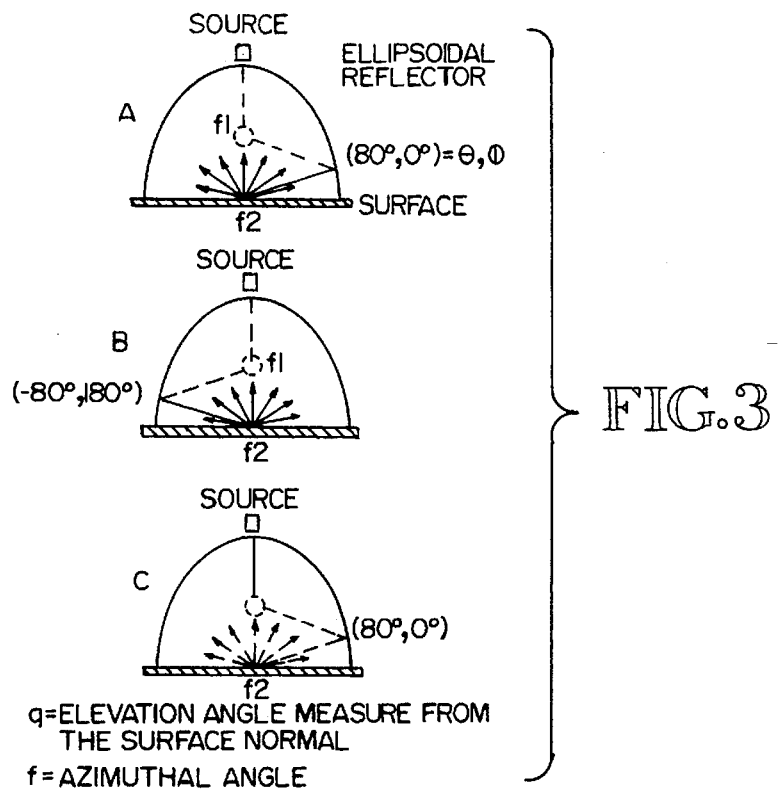
FIG. 3(A–C) illustrate reflection of the incident beam off the ellipsoid side walls showing an A & B full hemisphere imaging.

For an isotropic surface, for which all azimuthal orientations are equivalent, e.g. typical paints, it is sufficient to collect only half of the diverging rays if the symmetry of the problem is exploited. The IR beam which illuminates the sample at the lower focus 12, must travel in a plane which passes through the lower focus and is perpendicular to both the sample surface and the plane of the figure (end views are shown in FIGS. 3-A and 3-B). If the surface is not isotropic, complete hemispherical reflectance data can be obtained by making an additional measurement in which the beam orientation remains fixed relative to the sample surface but the instrument azimuth angle is rotated by 180° (FIG. 3-C illustrates this rotation).

Figure 2:
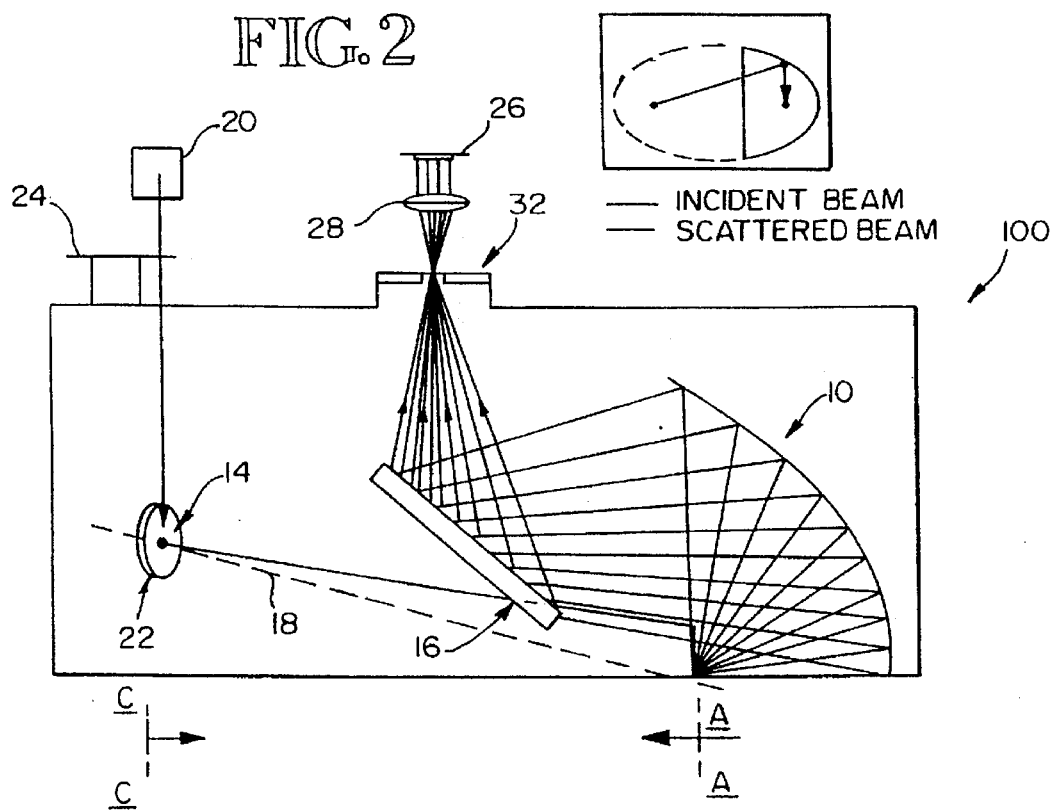
FIG. 2 is a schematic side elevation of a preferred reflectometer of the present invention.

The illumination scheme shown in FIGS. 2 and 3 also utilizes the properties of the ellipsoid. An IR source 20, such as a blackbody, glow bar, or lamp is collimated to form a beam which is directed onto a mirror 22 located at the upper focus 14. The beam passes through a hole in the secondary mirror 16 and strikes the ellipsoidal reflector 10 which relays the beam to the lower focus 12 on the sample. With a gimbal mirror 22 which pivots on the upper focus 14 and an appropriate slot in the secondary mirror, the angle of incidence can be varied from normal to near grazing (>80°). A second slot or hole is needed to allow fixed illumination when the device is turned 180° for measuring non-isotropic surfaces (FIG. 3-C). This would probably also entail a translation of the secondary mirror to shift the unused hole to avoid losing the specular reflection of the beam.

One way to obtain hemispherical reflectance data is to allow the reflected rays to converge onto a large-area single-element IR detector. In the absence of the illuminating beam, the detector signal is proportional to the sum of the self-emitted and reflected radiation from the sample surface. If the measuring device is in thermal equilibrium with the sample, the total IR energy leaving the sample surface would equal that of a blackbody at the same temperature. When the illuminating beam is turned on, the change in detector signal is attributable to the specular and diffuse reflections of interest. In practice, this measurement will require chopping of the beam 24 and subtraction of the two detector signal levels to determine the desired reflectance.

Figure 4:
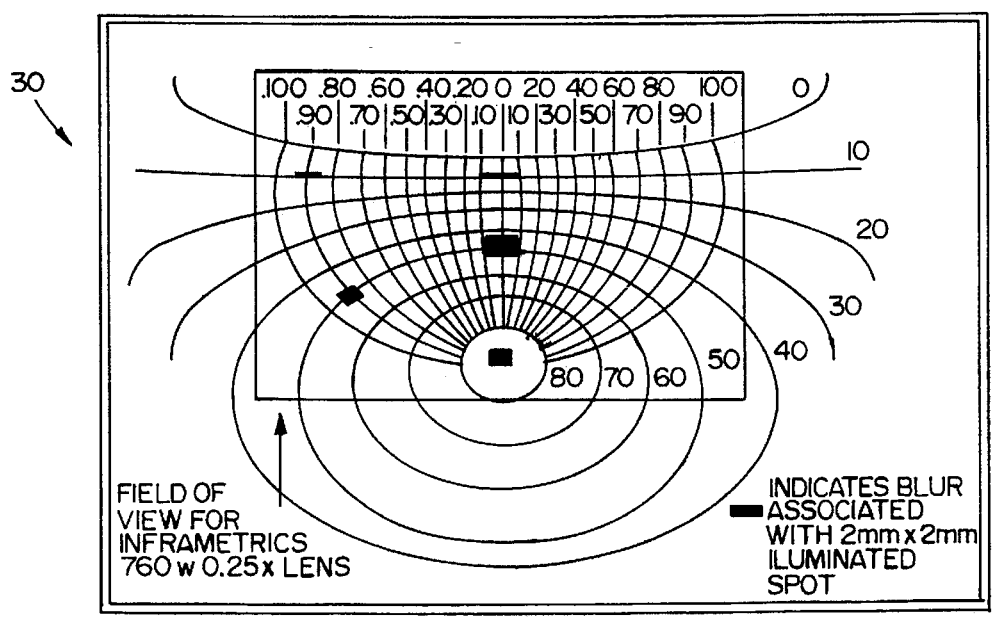
FIG. 4 is a graph showing mapping of angle space onto a 2-D plane.

The single detector approach provides a simple integrated number but ignores valuable information related to the details of the angular distribution of the reflected light. Such information can readily be obtained in the form of an image by using an IR focal plane array 26 or a scanning type imager. If the illuminating beam at the lower focus was of negligible extent, an image of the angular distribution is formed simply by displacing the detector plane in front or in back of the image focus. For an illumination spot of finite extent and an array of reasonable size, an image formed in this manner would have poor angular resolution. By using an appropriate lens 28, we can observe the far-field distribution pattern in the detector plane. As with the single detector, we use beam chopping and image subtraction to obtain the desired distribution. The cold aperture 32 is maintained at a low temperature with liquid nitrogen to reduce emitted IR radiation impinging on the array. While the energy distribution in these images will vary with sample material and angle of incidence, the grid 30 representing the mapping of angle space onto a 2-D plane will remain fixed. An optical raytrace code was used to determine the shape of this grid and it is shown in FIG. 4. The particular geometry corresponds to a focus separation of 3 in and the upper focus 1 in higher than the lower focus. The calculation assumes that the reflector surface extends well beyond the half hemisphere of interest. The grid lines are marked according to elevation angle and azimuth angle. For typical arrays and imagers, the output video image is inverted and flipped left-to-right leading to a image that resembles the view from the inside of a globe. For reference, a box corresponding to the field of view achievable by an Inframetrics 760 imager with a 0.25×lens is shown.

FIG. 4 also shows some representative blur spots associated with a square 2 mm-by-2 mm illumination spot. In each case, the blur represents the locus of points in the image associated with rays leaving the spot at a uniform angle. These size of these blurs are expected to be limited by the size of the lens entrance pupil on the Inframetrics 760 imager. These results include only those aberrations introduced by the finite illumination spot geometry and the ellipsoidal reflector. Some additional aberration will result from the lens system used to create the far-field pattern.

A single number for the half-hemispherical reflectance can be obtained by adding up the intensity that falls within the +90° and −90° azimuth and the 0° to 90° elevation contours. Since typical arrays and imagers provide standard video outputs, there are many available choices of computer hardware software to support the video image subtraction and processing. If desired, computer processing can remap the grid 30 to a more convenient shape, compute statistics describing the reflection or automatically compare the measured distribution with a stored ideal distribution to determine whether it is within allowed tolerance. With computer control over data acquisition and any moving parts in the device, we can make a rapid assessment of the bidirectional reflectance for incidence angles between normal and grazing. If reference samples are available, we make direct comparisons between coatings to negate any concerns about calibration drift. Also, we can use calibration samples such as diffuse and specular gold to verify proper operation of the measurement system.

We have completed design analysis on the baseline concept which demonstrates its feasibility and measure of expected performance. The specific configuration of the baseline shown in FIG. 2 is only one of many alternate designs which could provide angle-space imaging of the directional scatter. The device uses a reflector and/or lens system to collect the light from a large solid angle and subsequently images the far field distribution pattern. Other reflector and illumination geometries or the use of lenses may also be suitable depending upon need and the desired level of sophistication.

Figure 5:
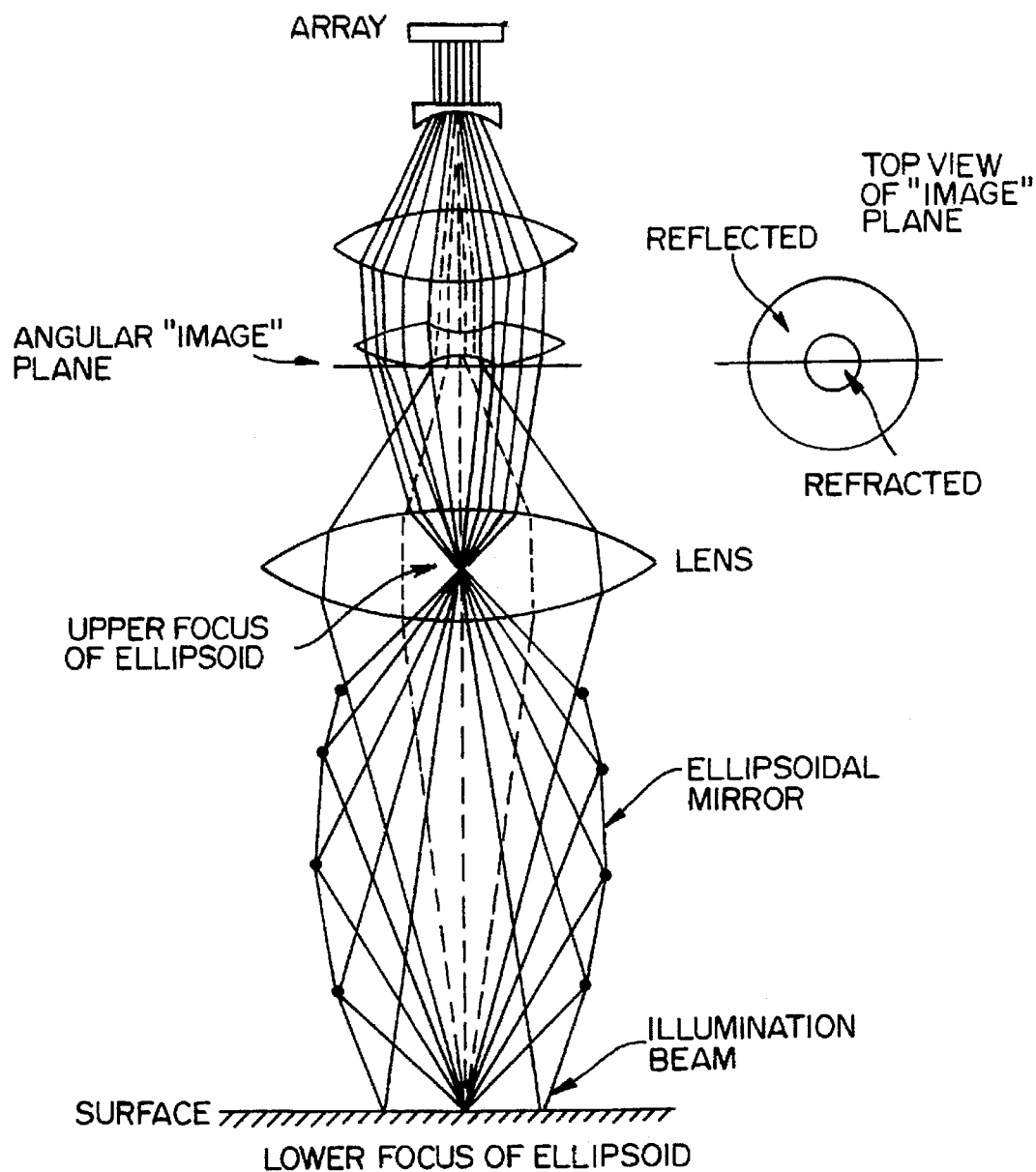
FIG. 5 is an alternate embodiment using an ellipsoid reflector and a series of lenses.
Figure 8:
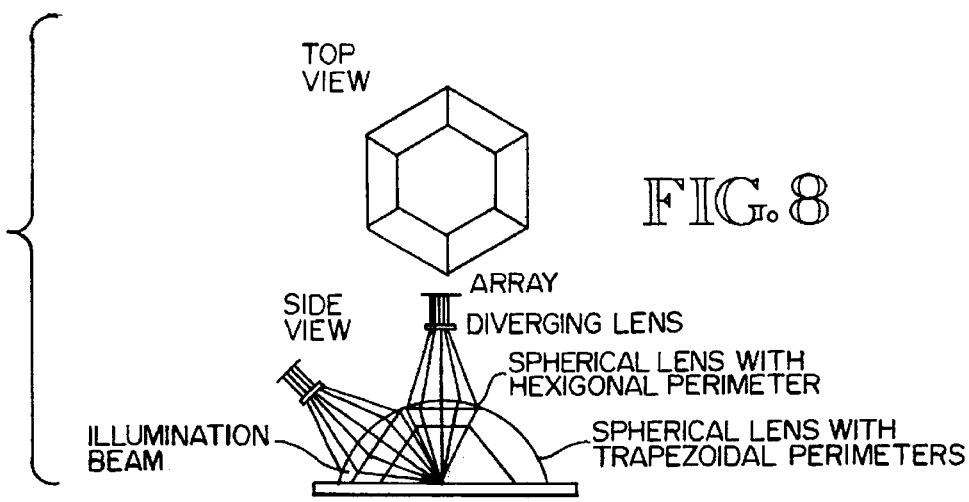
FIG. 8 illustrates a variation using hexagonal lenses.
Figure 9:
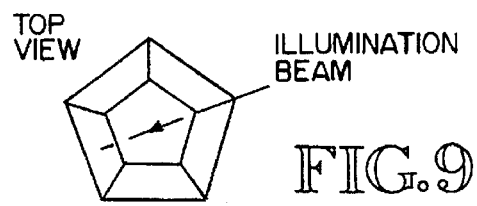
FIG. 9 illustrates another variation using pentagonal lenses.
Figure 10:
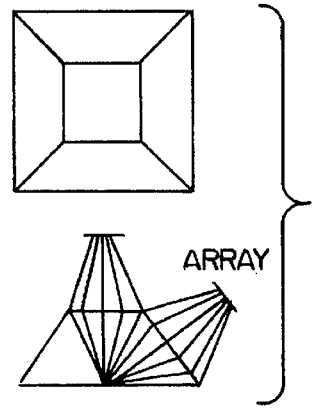
FIG. 10 illustrates a variation using square lenses.

The alternate designs may offer optimum measurement system for NDE applications. In particular, the concept shown in FIG. 5 provides full hemispherical coverage and no moving parts. It should also be relatively easy to keep clean. This design is perhaps the most elegant, as well as robust.

The device in FIG. 5 is based on an ellipsoid reflector (cut off at both ends) and a series of lenses. In this concept, one end of the cut-off ellipsoid reflector sits on the surface. The illumination beam is brought in through the side wall of the ellipsoid reflector. Reflected radiation is separated (by the combined effects of the ellipsoid reflector and lens) into two distinct areas at the angular "image" plane: (1) in FIG. 5 the radiation which is scattered from the sample at angles between 90° and 15° is reflected off the wall of the ellipsoid reflector; these rays pass through the lens with limited change in direction; and (2) the radiation scattered from the surface directly onto the lens is focused by the lens toward a focal point beyond the angular "image" plane.

The angular "image" in this plane is shown as a doughnut-shaped section (reflections into angles between 15° and 90° in elevation (relative to the surface normal)) and a center section (reflections into angles between 0° and 15° in elevation).

From the angular "image" plane the radiation is collected by a lens which has two sections, a positive (convex) lens and a negative (concave) lens. We can make this lens by cutting a hole in the convex lens and mounting the concave lens in the center or we could use a special optic lens. Radiation emerges parallel from this lens, and is reduced by a series of two lenses (Galilean telescope) to fit on a small detector array. In summary, our device provides full hemispherical "imaging" with sufficient angular resolution. The conceptual design appears to fit within size constraints, involve no moving parts (unless it is desired to change incident angle), and involves only one standard detector array (or single detector for collection of total hemispherical reflectance).

Concepts illustrated in FIGS. 6 & 7 are variations of the baseline design (FIG. 2). These variations are included to illustrate the different advantages available with slight modifications to the baseline design. In FIG. 6 the incident IR beam is injected through the ellipsoid wall of the reflector and the detector array is included just beyond the upper focus of the ellipsoid reflector.

The device in FIG. 7 uses a 50/50 beamsplitter in place of the secondary mirror to allow the incident beam to pass through the beamsplitter at any desired angle without the need to put holes or slots in the mirror.

Figure 11:
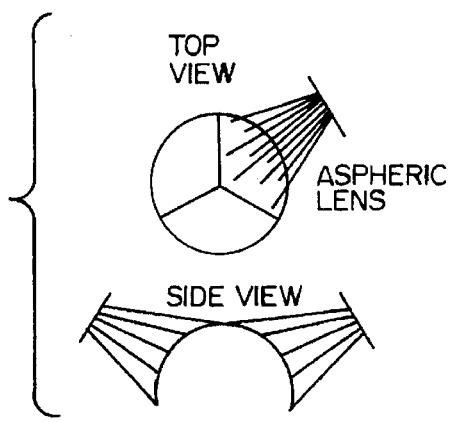
FIG. 11 illustrates a variation using refraction of the scattered radiation by an array of three shaped lenses.
Figure 12:
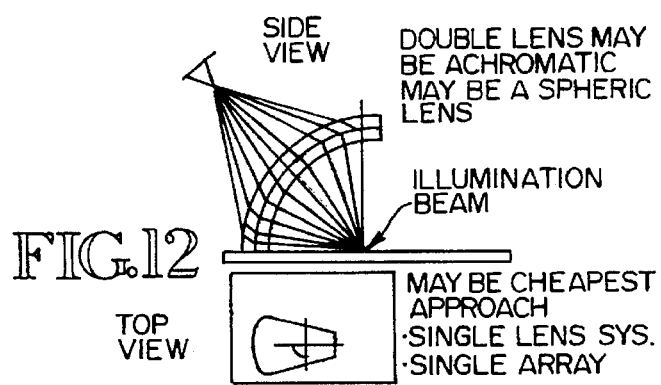
FIG. 12 illustrates a final variation using a single rotating lens to obtain full hemispherical coverage.

Concepts illustrated in FIGS. 8–12 are based on the refraction of the scattered radiation by a shaped lens array with as few as three lenses (FIG. 11). In these concepts, the lenses cover the hemisphere and each lens focuses the radiation from the sample onto an array set slightly away from the lens focus. Each of these lens systems could be fixed or reduced in the number of lenses and rotated. The device in FIG. 12 may be the cheapest, using only a single lens and array. In this concept the lens rotates about the vertical axis to provide full hemispherical coverage.

While described with reference to IR radiation, the concepts apply to other frequencies.

The device accomplishes the following unique functions:
1. The configuration of an array or other imaging detector viewing/measuring the far-field angular distribution of light reflected from the surface;
2. The concept of integrating the far-field angular distribution by summing, or by replacing the array/imager with a single detector, so as to obtain the total hemispherical reflectance;
3. The device functions as a light-gathering system which is a combination of an ellipsoid and lens system which gathers 2 distinct classes of light rays: rays reflecting from the surface and then off the ellipsoid mirror, and rays reflecting directly from the surface to be measured forming an annular ring pattern in the plane of a "bifocal" lens, including:
   (a) an ellipsoidal mirror with two ends cut-off, one end is cut so that the surface to be measured is perpendicular to the major axis of the ellipsoid, and the surface passes through one of the ellipsoid foci;
   (b) a simple or compound lens which is centered at the second ellipsoid focus and is sized large enough to collect those rays which do not interact with the ellipsoidal mirror;
   (c) formation of an angular image plane;
   (d) rays arriving at the angular image plane are of two classes:
      (i) rays reflecting directly from the measured surface and forming the central core of the image, not interacting with the ellipsoidal mirror, and
      (ii) those rays reflecting off of the measured surface and then off of the ellipsoidal mirror which fill the annular ring of the image;
   (e) a special "bifocal" lens or lens system placed at the image plane which is diverging to the core rays and converging to the rays in the annular ring, so as to make all rays exiting the angular image plane very nearly parallel.
   (f) a reducing telescope to match the rays exiting the angular image plane to the selected sensor array or other imager or a single detector; and
   (g) the light beam can illuminate the surface to be measured over a wide range of angle, including near grazing angles.
4. Alternate embodiments use lens arrays (with as few as three lenses) in conjunction with detector arrays or other imagers to form images of the angular distribution of light scattered from the surface.
5. A single lens and detector array can be rotated about an axis so as to scan the angular distribution of light reflected from the surface.

While we have described preferred embodiments, those skilled in the art will readily recognize alterations, variations, and modifications which might be made without departing from the inventive concept. Therefore, interpret the claims liberally with the support of the full range of equivalents known to those of ordinary skill based upon this description. The examples illustrate the invention and not intended to limit it. Accordingly, limit the claims only as necessary in view of the pertinent prior art.

We claim:

1. A directional reflectometer for measuring the optical bidirectional reflectance of a surface, comprising:
   (a) a source of light in a frequency range of interest;
   (b) an ellipsoid reflector having an upper and lower focus and positioned to receive light from the source;
   (c) a gimbaled mirror at the upper focus of the reflector for light to the reflector for scanning the surface at the lower focus;
   (d) a secondary mirror for redirecting reflected light from the surface of the reflector;
   (e) a cold aperture positioned substantially at the focus of the secondary mirror;
   (f) an array detector for viewing the reflected light from the secondary mirror passing through the cold aperture and for creating a signal proportional to the reflected light; and
   (g) computing means for analyzing the signal of the reflected light to compute the bidirectional reflectance.

2. The reflectometer of claim 1 wherein the frequency range is about 3–12 μm.

3. The reflectometer of claim 1 wherein the frequency range is about 0.3–3 μm.

4. The reflectometer of claim 1 further comprising a Galilean telescope positioned between the cold aperture and the array detector in the path of the reflected light for reducing the beam of reflected light onto the array detector.

5. The reflectometer of claim 4 further comprising a diverging lens substantially at the cold aperture and an angular image plane lens positioned in the light path between the diverging lens and the Galilean telescope, the angular image plane lens having a convex lens periphery surrounding a concave lens center section.

6. The reflectometer of claim 4 wherein the secondary mirror is a beamsplitter for allowing the incident light to pass from the gimbaled mirror to the reflector without the need for holes or slots.

7. The reflectometer of claim 1 wherein the secondary mirror is a beamsplitter for allowing the incident light to pass from the gimbaled mirror to the reflector without the need for holes or slots.

8. The reflectometer of claim 1 wherein the source of light is adjustable in its angle of incidence on the surface from normal to about 80° off normal.

9. The reflectometer of claim 1 wherein the source of light is a black body source.

* * * * *

UNITED STATES PATENT AND TRADEMARK OFFICE
CERTIFICATE OF CORRECTION

PATENT NO. : 5,637,873
DATED : June 10, 1997
INVENTOR(S) : Keith J. Davis, et al.

It is certified that error appears in the above-identified patent and that said Letters Patent is hereby corrected as shown below:

Column 1, Line 4, please insert the following:

-- This invention was made with Government support under Contract F33615-95-C-5237 awarded by the Air Force. The Government has certain rights in this invention. --

Signed and Sealed this

Twenty-ninth Day of August, 2000

*Attest:*

Q. TODD DICKINSON

*Attesting Officer*     *Director of Patents and Trademarks*